United States Patent [19]
Torgerson et al.

[11] Patent Number: 5,876,421
[45] Date of Patent: Mar. 2, 1999

[54] RESIDUAL XYLENE REMOVAL FROM SUTURES

[76] Inventors: Robert D. Torgerson, 1 Rollwood Dr., Guilford, Conn. 06437; Ross R. Muth, 97 Clearview Dr., Brookfield, Conn. 06804

[21] Appl. No.: 823,709

[22] Filed: Mar. 25, 1997

[51] Int. Cl.$^6$ .................................................. A61B 17/04
[52] U.S. Cl. ........................... 606/228; 606/230; 606/231
[58] Field of Search .................................... 606/228, 229, 606/230, 231

[56] References Cited

U.S. PATENT DOCUMENTS

| | | | |
|---|---|---|---|
| 3,187,752 | 6/1965 | Glick | 128/335.5 |
| 3,424,164 | 1/1969 | Bloch et al. . | |
| 3,629,310 | 12/1971 | Bailey et al. . | |
| 3,736,646 | 6/1973 | Schmitt et al. . | |
| 3,757,786 | 9/1973 | Smith . | |
| 4,027,676 | 6/1977 | Mattei | 128/335.5 |
| 4,185,637 | 1/1980 | Mattei | 128/335.5 |
| 4,201,216 | 5/1980 | Mattei | 128/335.5 |
| 4,532,929 | 8/1985 | Mattei et al. | 128/335.5 |
| 4,617,340 | 10/1986 | Tanaka et al. . | |
| 5,304,205 | 4/1994 | Shinoda et al. . | |
| 5,383,903 | 1/1995 | Totakura . | |

OTHER PUBLICATIONS

*HULS Silicon Compounds Register and Review, Silanes and Silicones for Creative Chemists,* 5th Edition; 1991 Huls America, Inc. Piscataway, NJ; p. 276.

*Primary Examiner*—Michael Powell Buiz
*Assistant Examiner*—Tina T. D. Pham

[57] ABSTRACT

A method for removing residual xylene from sutures includes contacting the suture with water either subjecting the suture to an atmosphere containing water vapor or be immersing the suture in liquid water, followed by drying the suture.

17 Claims, No Drawings

RESIDUAL XYLENE REMOVAL FROM SUTURES

TECHNICAL FIELD

The present disclosure relates to a method for removal of residual xylene from sutures, particularly braided silk sutures.

BACKGROUND OF RELATED ART

Many synthetic materials are presently used as surgical sutures. These materials may be used as single filament strands, i.e., monofilament sutures, or as multifilament strands in a braided, twisted or other type of multifilament construction. Synthetic sutures have been made from materials such as polypropylene, nylon, polyamide, polyethylene, polyester such as polyethylene terephthalate, and segmented polyether-ester block copolymers. In addition, absorbable synthetic sutures have been prepared from synthetic polymers such as polymers containing glycolide, lactide, dioxanone and/or trimethylene carbonate.

Natural materials have also been used to make sutures. For example, silk has been used to make nonabsorbable sutures. As another example, catgut sutures are absorbable sutures made from a natural material.

Sutures used for the repair of body tissues are placed in intimate contact with the tissue and, frequently, completely within the body. Thus, sutures may not contain components that are irritating to body tissue. Accordingly, any tissue-irritating components used during manufacture of the suture must be stringently removed from the suture prior to use.

For example, ethylene oxide has been used to sterilize sutures and other surgical devices. However, since ethylene oxide is an irritant to human tissue, stringent removal of any residual ethylene oxide is required before the suture packages are sealed.

As another example, xylene has been used in the processing of suture material as a solvent for suture coating materials employed to improve the handling characteristics such as knot-run-down to reduce frictional chatter and fraying. In U.S. Pat. No. 3,187,752 xylene is used as a solvent for applying polymeric silicone to a braided silk suture. In U.S. Pat. No. 4,185,637 a poly (p-dioxanone) braided suture is coated with a gelatinous dispersion of calcium stearate in xylene.

Xylene is not soluble in water and is irritating to human body tissue. Thus, if xylene is used (e.g., as a solvent) at any point in a process for making a surgical device, any residual xylene must be removed prior to use, preferably prior to packaging.

It would be desirable to provide an easy and efficient method for removing residual xylene from a suture or other surgical device.

SUMMARY

A method is provided herein for treating a surgical device (e.g., suture material) to remove xylene therefrom. The method includes the steps of contacting a suture containing xylene with water, either as liquid or vapor, at a temperature of from about 20° C. to about 150° C., preferably from about 40° C. to about 90° C., for at least about 2 hrs., then drying the suture. For example, the water can be in the form of water vapor in an atmosphere surrounding the suture having a relative humidity of from about 70% to about 100%. Alternatively, the water can be in a liquid state, the suture being immersed in a bath thereof. Drying the suture is preferably accomplished under reduced pressure, i.e. in, preferably for at least about 6 hours and under elevated temperatures, such as, for example, from about 35° C. to about 60° C.

DETAILED DESCRIPTION

The method described herein may be used with any type of surgical device containing xylene. Thus, while the embodiments herein will be described with respect to sutures, it should be understood that residual xylene can be removed from other known surgical devices as well. Moreover, the residual xylene can be removed from any type of suture. For example, the suture can be made from synthetic bioabsorbable materials such as polymers of glycolide, lactide, caprolactone, trimethylene carbonate and/or p-dioxanone; natural materials such as gut or silk; and non-bioabsorbable synthetic materials such as polypropylene, nylon, polyamide, polyethylene, and polyesters. The suture can be monofilament or multifilament. When more than one filament is used the filaments may be braided, twisted, entangled, intertwined, or arranged in some other multifilament configuration. In particularly useful embodiments the present methods are employed with silk, nylon or polyester sutures.

The presence of residual xylene in the surgical device can result from any processing steps used to fabricate the surgical device. Most commonly, however, the residual xylene will result from the application of a coating material. That is, xylene can be used as part of a solvent system into which a coating material is dissolved or suspended. Once the xylene based solution or suspension is applied to the surgical device, simply drying the suture will remove the majority of the xylene from the surgical device. However, as mentioned above, due to the incompatibility of xylene with human tissue, strict removal thereof is required.

Sutures with coatings containing an organo-silicon compound (such as silicone) in xylene. Other components may also be employed in the coating. Accordingly, the description given herein is intended to be illustrative and not limiting.

The method includes subjecting a coated braided suture to warm water, either by surrounding the suture in water vapor in a heated humid atmosphere or by immersing the suture in a bath of heated liquid water. When a humid atmosphere is employed, the relative humidity can range from about 70% to about 100%, preferably about 80% to about 90%. Treatment of the suture with humid atmosphere or liquid water is preferably performed at a temperature of from about 20° C. to about 150° C., and more preferably from about 40° C. to about 90° C. The exposure to the humid atmosphere is preferably performed for at least about 2 hours, more preferably at least about 12 hours.

Alternatively, the surgical device can be soaked in water. The water bath should be at a temperature in the range of about 20° C. to about 150° C., preferably about 40° C. to about 90° C. The water soak can last for a period of time ranging from about 2 hours to about 24 hours or longer, preferably about 4 hours to about 6 hours.

The amount of residual xylene is preferably reduced to below about 50 ppm, more preferably below about 20 ppm, and most preferably below about 10 ppm. The exact combination of conditions necessary to achieve these results depends upon a number of factors, including the physical structure of the surgical device (e.g., monofilament vs. multifilament sutures) and the amount of residual xylene initially present.

After exposure to water, the surgical device is dried. The drying is preferably performed at reduced pressure and elevated temperature (e.g., about 35° C. to about 60° C.) and optionally with purging in a flow of dry nitrogen.

The examples below are illustrative of sutures treated in accordance with the present method. In Examples 1–4 braided silk sutures (size 2) were coated with a 3% by weight solution of silicone (commercially available as NuSil MED 2245 Part A from NuSil Technology, Carpinteria, Calif.) in xylene. The coating was applied by passing the sutures through a bath containing the coating solution then allowing the sutures to dry by evaporation. Thereafter, the sutures were treated in accordance with the method described herein to remove residual xylene. The amount of residual xylene was measured before and after treatment.

EXAMPLE 1

A spool of multifilament silk suture with a coating applied as described above was tested for xylene content and found to have an initial residual xylene content of 168 ppm. The suture was then placed in an oven having a controlled atmosphere of about 82% humidity at about 60° C. for about 24 hours. The suture was then dried for about 24 hours under reduced pressure (less than about 2 Torr) with mild heat (30° C.) and with a nitrogen purge. The suture was again tested and found to have a final residual xylene content of 3.16 ppm.

EXAMPLE 2

A spool of multifilament silk suture with a coating applied as described above was tested for xylene content and found to have an initial residual xylene content of about 152 ppm. The suture was then placed in an oven having a controlled atmosphere of about 82% humidity at about 60° C. for about 24 hours. The suture was then dried for about 24 hours under reduced pressure (less than about 2 Torr) with mild heat (30° C.) and with a nitrogen purge. The resulting suture was again tested and found to have a final residual xylene content of 1.38 ppm.

EXAMPLE 3

A spool of multifilament silk suture with a coating applied as described above was tested for xylene content and found to have an initial residual xylene content of about 144 ppm. The suture was then placed in an oven having a controlled atmosphere of about 82% humidity at about 60° C. for about 48 hours. The suture was then removed and tested, and found to have a residual xylene content of 10.3 ppm. The suture was then dried for 24 hours under reduced pressure (less than about 2 Torr) with mild heat (30° C.) and with a nitrogen purge. The resulting suture was again tested and found to have a final residual xylene content of about 0.6 ppm.

EXAMPLE 4

A spool of multifilament silk suture with a coating applied as described above was tested for xylene content and found to have an initial residual xylene content of about 139 ppm. The suture was then placed in an oven having a controlled atmosphere of about 82% humidity at about 60° C. for about 48 hours. The suture was then removed, tested and found to have a xylene content of 12.3 ppm. The suture was then dried for 24 hours under reduced pressure (less than about 2 Torr) with mild heat (30° C.) and with a nitrogen purge. The resulting suture was again tested and found to have a final residual xylene content of about 0.48 ppm.

EXAMPLE 5

A spool of multifilament silk suture with a coating applied as described above was tested for xylene content and found to have an initial residual xylene content of 157 ppm. The suture was then immersed in water at about 60° C. for about 4 hours. The suture was then removed from the water and dried for about 24 hours under reduced pressure (less than about 2 Torr) with mild heat (30° C.) and with a nitrogen purge. The suture was tested and found to have a residual xylene content of 5.06 ppm.

EXAMPLE 6

A spool of multifilament silk suture with a coating applied as described above was tested for xylene content and found to have an initial residual xylene content of 157 ppm. The suture was then immersed in water at about 60° C. for about 6 hours. The suture was then removed from the water and dried for about 24 hours under reduced pressure (less than about 2 Torr) with mild heat (30° C.) and with a nitrogen purge. The suture was tested and found to have a residual xylene content of 20 ppm.

EXAMPLE 7

A spool of multifilament silk suture with a coating applied as described above was tested for xylene content an found to have an initial residual xylene content of 157 ppm. The suture was then immersed in water at about 60° C. for about 24 hours. The suture was then removed from the water and dried for about 24 hours under reduced pressure (less than about 2 Torr) with mild heat (30° C.) and with a nitrogen purge. The suture was tested and found to have a residual xylene content of 10.5 ppm.

The above results show that exposure of the suture to a humid atmosphere or water bath followed by drying reduces residual xylene content to an acceptable degree. The reduction in xylene using the present process does not adversely affect the amount of silicone coating applied to the suture. Thus, the sutures maintain excellent handling characteristics. The effectiveness of moisture in removing xylene is quite a surprising discovery in view of the respective immiscibility of water and xylene. Reduced residual xylene content provides a suture with superior compatibility with body tissue.

It will be understood that various modifications may be made to the embodiments disclosed herein. Therefore, the above description should not be construed as limiting, but rather as exemplifications of preferred embodiments. Those skilled in the art will envision other modifications within the scope and spirit of the claims appended hereto.

What is claimed is:

1. A method for treating a surgical device to remove xylene therefrom, comprising:

contacting a surgical device containing xylene with water at a temperature of from about 20° C. to about 150° C. for at least about 2 hours; and, drying the device, whereby the amount of xylene contained by the device is reduced.

2. The method of claim 1 wherein the amount of xylene contained in the surgical device is reduced to below about 50 ppm.

3. The method of claim 1 wherein the amount of xylene contained in the surgical device is reduced to below about 20 ppm.

4. The method of claim 1 wherein the amount of xylene contained in the surgical device is reduced to below about 10 ppm.

5. The method of claim 1 wherein the surgical device is a multifilament suture.

6. The method of claim 5 wherein the suture is silk.

7. The method of claim 1 wherein the surgical device is immersed in the water.

8. The method of claim 1 wherein the step of drying the surgical device comprises subjecting the surgical device to reduced pressure.

9. The method of claim 7 wherein the step of drying the surgical device is performed at an elevated temperature.

10. The method of claim 9 wherein the step of drying the surgical device is performed at a temperature of from about 35° C. to about 60° C.

11. The method of claim 1 wherein the step of contacting the device with water is conducted at a temperature of from about 50° C. to about 70° C.

12. The method of claim 1 wherein the step of contacting the surgical device with water lasts for at least about 4 hours.

13. The method of claim 1 wherein the step of contacting the surgical device with water lasts for at least about 6 hours.

14. The method of claim 1 wherein the step of contacting the surgical device with water lasts for at least about 24 hours.

15. The method of claim 5 wherein the suture is made from nylon.

16. The method of claim 5 wherein the suture is made from polyester.

17. The method of claim 1 wherein the water is at a temperature of about 40° to about 90° C.

* * * * *